(12) United States Patent
Veeger et al.

(10) Patent No.: US 7,241,452 B2
(45) Date of Patent: Jul. 10, 2007

(54) SKIN AND HAIR CARE AGENTS

(75) Inventors: Marcel Veeger, Goch (DE); Andreas Klotz, Grevenbroich (DE); Gerda Maehse, Krefeld (DE); Beatrice Haeusler, Krefeld (DE); Karin Faensen, Kerkrade (NL)

(73) Assignee: Stockhausen GmbH & Co. KG, Krefeld (DE)

( * ) Notice: Subject to any disclaimer, the term of this patent is extended or adjusted under 35 U.S.C. 154(b) by 45 days.

(21) Appl. No.: 10/489,596

(22) PCT Filed: Sep. 20, 2001

(86) PCT No.: PCT/EP01/10903

§ 371 (c)(1),
(2), (4) Date: Aug. 3, 2004

(87) PCT Pub. No.: WO03/026609

PCT Pub. Date: Apr. 3, 2003

(65) Prior Publication Data

US 2004/0247557 A1    Dec. 9, 2004

(51) Int. Cl.
*A61K 6/00*   (2006.01)
*A61K 8/02*   (2006.01)

(52) U.S. Cl. ................................ 424/401
(58) Field of Classification Search ............ None
See application file for complete search history.

(56) References Cited

U.S. PATENT DOCUMENTS 6,376,438 B1 * 4/2002 Rosenberger et al. ....... 510/139

FOREIGN PATENT DOCUMENTS

| DE | 198 43 547 | | 4/1999 |
|----|------------|---|--------|
| DE | 198 14 980 | | 10/1999 |
| WO | 99/22712 | | 5/1999 |
| WO | WO 99/22712 | * | 5/1999 |

* cited by examiner

Primary Examiner—Michael Woodward
Assistant Examiner—Bethany Barham
(74) Attorney, Agent, or Firm—Oblon, Spivak, McClelland, Maier & Neustadt, P.C.

(57) ABSTRACT

Random three- and four-amino acid copolymers having lengths of 14-, 35- and 50-amino acid residues are provided. Fifty-mers of FEAK were effective inhibitors of MBP 85-99 or proteolipid protein (PLP) 40–60-specific HLA-DR-2-restricted T cell clones. These copolymers efficiently suppressed EAE induced in susceptible SJL/J (H-2s) strain of mice with either whole spinal cord homogenate (WSCH) or with the encephalitogenic epitope PLP 139-151. YFAK 50-mer having a molar ratio of about y 0.8:F 0.2 inhibited binding of biotinylated MBP 85-99 epitope to HLA-DR-2 molecules more efficiently than either unlabeled MBP 85-99 or Copaxone®. YFAK and FAK copolymers efficiently suppressed EAE induced in SJL/J (H-2s) mice with the encephalitogenic epitope PLP 139-151. Copolymers YFK, VYAK and tryptophan-containing VWAK were efficacious in alleviating severity and duration of symptoms of EAE induced by MBP 85-99, in a humanized mouse model expressing genes for both an HLA-DR-2 linked to multiple sclerosis (MS) in humans and for a T cell receptor from an MS patient.

21 Claims, No Drawings

SKIN AND HAIR CARE AGENTS

The invention relates to hydrous skin and hand cleansing agents, especially so-called waterless handcleaners having improved dermatological compatibility, and to the use of said agents for removing extreme soiling.

Skin and hand cleansing agents are extensively used in the industry, especially in those cases where tenacious soiling occurs, which is caused by lacquers, fats, oils, lubricants, metal dusts, graphite, soot and the like.

Such cleansing agents are per se known as so-called coarse handcleaners (cf., H. Tronnier, J. Kresken, K. Jablonski, B. Komp, "Haut und Beruf", Grosse Verlag, Berlin, 1989, pp. 75–108). In general, these are formulations including an abrasive, surfactant/surfactant mixtures, thickening agents, and optionally auxiliary agents to control consistency, appearance, odor, and stability, such as pigments, odorous substances, stabilizers, and preservatives. In case of particularly tenacious soiling, there are products where the use of the above-mentioned ingredients is insufficient. Such formulations are added with organic solvents such as aliphatic hydrocarbons, terpenes, carboxylic esters of the dimethyl adipate, dimethyl glutarate, dimethyl succinate (DBE), and di-n-butyl adipate or diisopropyl adipate types such as described in DE 43 35 933 A1.

In this context, reference is made to the so-called waterless cleaners available on the market, the good cleansing effect of which is predominantly based on the above-mentioned organic solvents, particularly benzines, kerosenes, and short-chain paraffin oils. Thus, commercially available waterless cleaners have the following composition:

| | |
|---|---|
| Petroleum distillates: | 35.0 to 45.0 wt. % |
| Water: | 30.0 to 35.0 wt. % |
| Mineral oils: | 10.0 to 20.0 wt. % |
| Sodium oleate: | 10.0 to 20.0 wt. % |
| Trideceth-9: | 1.0 to 5.0 wt. % |
| Propylene glycol: | 1.0 to 5.0 wt. % |
| Petrolatum: | 1.0 to 5.0 wt. % |
| Lanolin: | 1.0 to 5.0 wt. % |
| Zinc pyrithione: | 0.1 to 1.0 wt. % |

Zinc pyrithione: 0.1 to 1.0 wt.-%

Further examples of such solvent-containing "waterless cleaners" can be found in Ernest W. Flick, "Cosmetic and Toiletry Formulations", Second Edition, 1989, pp. 737–744. Such coarse handcleaners are used without addition of water, cleansing exclusively being effected by means of the product and a drying cloth.

Referring to the industrial sector, the more frequently such products are applied on the skin (up to 6 times per day and more), the more clearly the detrimental effects of surfactants and particularly solvents come to the fore, namely, defatting and dehydration of the skin by destroying the hydro-lipid mantle of the skin. As a result, there is enhanced absorption of toxic and allergenic substances or infestation by microorganisms, or, as a consequence, toxic or allergic skin reactions occur.

WO 99/06021 describes hydrous waterless handcleaner formulations having a water content of from 75 to 99 wt.-%, up to 25 wt.-% of a fatty acid ester or mixtures of such esters, and at least one surfactant. Especially in toxicological terms, such formulations represent a notable improvement over the above-mentioned products containing organic solvents. Nonetheless, improved skin compatibility and improved protection against skin dehydration are accompanied by a loss in cleansing efficiency compared to the solvent-containing waterless cleaners or solvent-containing coarse handcleaners.

DE 44 24 210 A1 describes waterless shower oils containing at least 45 wt.-% of an oil selected from the group of oils having a high content of triglycerides, saturated and/or unsaturated fatty acids, such as soya oil, sunflower oil, wheat germ oil, and 55 wt.-% at maximum of surfactants, preferably monoisopropanolaminelauryl ether sulfate (MIPA), laureth sulfate, laureth-4, and coconut fatty-acid diethanolamide. These formulations are disadvantageous in that their cleansing efficiency is not adequate to remove extreme soiling as demanded on coarse handcleaners. Moreover, these formulations include fatty acid mono- or diethanolamides which, according to Fiedler, Edito Cantor Verlag, 4th edn., 1996, p. 376, are known to involve a sensitization risk.

Hydrous shower formulations are known from EP 0 769 292 A1 wherein, in addition to surfactant mixtures, colza oil or colza oil derivatives are used as skin care components. Due to their lacking cleansing efficiency, these agents neither are suited as coarse handcleaners, and particularly because these shower formulations, with respect to the consumer's acceptance, must meet quite different demands as compared to the coarse handcleaners where the cleansing performance of the product is preeminent.

DE 197 48 921 A1 relates to hydrous, liquid, pasty or creamy hand cleansing agents, particularly coarse handcleaners including an abrasive, which agents have a content of 10 to 30 wt.-% of at least one vegetable oil selected from the group of triglycerides, saturated and/or unsaturated fatty acids, 10 to 30 wt.-% of at least one surfactant from the group of fatty alcohol ethoxylates, fatty alcohol ether sulfates and/or castor oil sulfonates, and 10 to 65 wt.-% of water, each time relative to the composition of the cleansing agent. Being coarse handcleaners, these agents include 1 to 30 wt.-% of at least one abrasive in the composition thereof. The coarse handcleaners described therein are highly skin-compatible in dermatological terms, inducing only minor dehydration of the skin even when used several times a day.

In view of the diverse fields of use, however, there is still a demand for skin and/or hand cleansing agents which are free of organic solvents and abrasives, have a cleansing efficiency comparable to that of solvent-containing cleansing agents in waterless use, i.e., as "waterless cleaners", and, when used together with water, show a cleansing efficiency comparable to those coarse handcleaners described in DE 197 48 921 A1, and at the same time, have good skin compatibility and low dehydration of the skin.

The object was therefore to provide such skin and hand cleansing agents, particularly coarse hand cleansing agents. Surprisingly, said object was accomplished by means of a skin and hand cleansing agent having a content of a) 10 to 60 wt.-%, relative to the composition of the cleansing agent, of one or more triglycerides, saturated and/or unsaturated fatty acids, b) 5 to 40 wt.-%, relative to the composition of the cleansing agent, of at least one fatty alcohol ethoxylate, c) 10 to 65 wt.-%, relative to the composition of the cleansing agent, of water, d) 0 to 30 wt.-%, relative to the composition of the cleansing agent, of one or more abrasives, e) optionally one or more viscosity-building agents, f) optionally further cosmetic adjuvants, additives and/or active substances, the sum of components a) through f) making 100 wt.-%.

The triglycerides, saturated and/or unsaturated fatty acids to be used according to the invention can be produced by synthesis or derived from naturally occurring oils, e.g. from animal fats or vegetable oils, the latter being subjected to an appropriate industrial treatment or purification for cosmetic uses. Vegetable oils are particularly preferred in this context. For example, preferred vegetable oils are dyer's safflower oil, olive oil, avocado oil, coconut oil, cotton seed oil, menhaden oil, palm seed oil, palm oil, peanut oil, soya oil, rape oil, linseed oil, rice palm oil, pine oil, sesame oil, wheat germ oil, cowslip oil, and sunflower oil. The oils can be used alone or as mixtures, with vegetable oils, especially colza oil, soya oil and/or linseed oil or a mixture thereof being particularly preferred.

The skin and hand cleansing agents according to the invention include 10 to 60 wt.-%, preferably 25 to 55 wt.-%, and more preferably 40 to 45 wt.-% of the above triglycerides, saturated, unsaturated fatty acids and/or mixtures thereof, and in a preferred embodiment, the triglycerides employed have a higher percentage of unsaturated fatty acids.

The fatty alcohol ethoxylates used as component b) preferably have the general formula $$R\text{---}O\text{---}(CH_2\text{---}CH_2\text{---}O)_nH$$

wherein

R=saturated, unsaturated, branched or unbranched alkyl residue, n=integer of from 1 to 11.

As to the saturated, unsaturated, branched or unbranched alkyl residue, it is preferred to use R=$C_8$ to $C_{18}$, particularly $C_{10}$ to $C_{16}$, and more preferably $C_{11}$ to $C_{14}$, where preferably n=3 to 6, particularly n=5 to 7.

The skin and hand cleansing agents according to the invention include 5 to 40 wt.-%, preferably 10 to 35 wt.-%, and more preferably 15 to 30 wt.-% of fatty alcohol ethoxylates, relative to the composition of the cleansing agent. In a preferred embodiment, the skin and hand cleansing agents according to the invention include 15 to 25 wt.-%, relative to the composition of the cleansing agent, of laureth-6 as fatty alcohol ethoxylate.

The inventive skin and hand cleansing agents free of organic solvents include 10 to 65 wt.-%, preferably 20 to 50 wt.-%, and more preferably 20 to 35 wt.-% of water, relative to the composition of the cleansing agent.

Although the skin and hand cleansing agents according to the invention have high cleansing efficiency, so that addition of abrasives to these cleansing agents is dispensable, the skin and hand cleansing agents may optionally include abrasives for particular cleansing applications. In this event, the percentage of abrasive or abrasives can be 1 to 30 wt.-%, preferably 10 to 20 wt.-%, relative to the composition of the cleansing agent. For example, abrasives to be used with preference are plastic abrasive agents based on polyethylene or polyurethane, abrasive agents based on natural stone and/or shell meals, particularly meals of walnut shells, almond shells, hazelnut shells, meals of olive, apricot or cherry stones, or any mixture of these shell and stone meals and beads of waxes, e.g. jojoba waxes, with hydrogen peroxide-bleached walnut shell meal being particularly preferred.

In another embodiment of the invention, the skin and hand cleansing agents include one or more viscosity-building agents such as organophilic and/or hydrophilic layer silicates, particularly bentonites, polysaccharides such as cellulose, guar meal and/or xanthans, modified polysaccharides, preferably cellulose ethers, carboxymethylcellulose and/or hydroxyalkylcelluloses, preferably hydroxyethylcellulose, and/or inorganic electrolytes, preferably sodium chloride and/or magnesium sulfate.

The skin and hand cleansing agents according to the invention may optionally include further cosmetic adjuvants, additives and/or active substances, e.g. pH regulators, stabilizers, preferably cetearyl alcohol and/or hydrogenated castor oils, such as trihydroxystearin, odorous substances, preservatives, preferably organic acids, and antioxidants such as vitamin E acetate. Preferably, oily or aqueous care components such as bisabolol, Aloe vera, panthenol, sodium PCA, jojoba oil etc. can also be used to emphasize the care effect.

The inventive skin and hand cleansing agents, especially coarse handcleaners, are produced in a batch or continuous process using well-known devices, the skin and hand cleansing agents preferably being obtained in the form of creamy agents or flowable viscous pastes. Suitable devices are heatable vessels equipped with stirrer, mixer and extruder.

The skin and hand cleansing agents of the invention are used in such a way that the cleansing agent is initially distributed over the skin, preferably without water, and subsequently wiped off without water, using a cloth, preferably a disposable article made of paper, plastic or textile fabric, etc. However, use with the aid of water is also possible, where the product is rinsed off together with the dirt. The former case concerns so-called "leave-on" products where good dermatological compatibility is particularly important, which is achieved when using the skin and hand cleansing agents according to the invention.

The inventive skin and hand cleansing agents, particularly coarse handcleaners, are used to remove coarse dirt strongly adhering to the skin, such as fats, oils and other lubricants, colors, lacquers, tar, graphite, soot, color pigments and similar substances as occur in the industrial and public sectors, in trade, in agriculture and in the household. When cleaning extremely tenacious soiling from lacquer, the skin and hand cleansing agents of the invention are particularly advantageous if the amount of triglycerides in the composition of the agents is higher than the amount of fatty alcohol ethoxylate, in which case the cleansing agent should include at least 15 wt.-% of fatty alcohol ethoxylate, relative to the composition.

Particularly preferred skin and hand cleansing agents are those agents which include at least 40 wt.-% of colza oil and at least 20 wt.-%, relative to the composition of the cleansing agent, of fatty alcohol ethoxylates, preferably laureth-6.

Despite the use of fatty alcohol ethoxylates which, above all, achieve the cleansing effect in the skin and hand cleansing agents of the invention, particularly in case of soiling from lacquer, but give rise to stronger dehydration of the skin in topical application and thus reduce the skin compatibility, it was surprising to find that, according to the invention, this can be compensated by higher levels of triglycerides. Without addition of mild surfactants such as fatty alcohol ether sulfates or sulfated castor oils necessarily required to be included in the handcleaner formulations described in DE 197 48 921, it was possible to achieve a cleansing effect of the inventive skin and hand cleansing agents in waterless application, i.e., as "waterless cleaners", which is comparable to that of solvent-containing cleansing agents, or, when used together with water, a cleansing efficiency comparable to those coarse handcleaners described in DE 197 48 921 A1, and at the same time, good skin compatibility and low dehydration of the skin, even though the skin and hand cleansing agents according to the invention are free of organic solvents and abrasives.

The invention will be illustrated with reference to the following examples and investigations, such as the skin compatibility trial using the Duhring chamber test, skin dehydration using a corneometer, and cleansing power using the hand wash test.

Test Methods

The skin compatibility trial is effected using the Duhring chamber test according to P. J. Frosch, A. M. Kligman, Contact Dermatites 5, p. 73, 1979; modified according to J. Kresken, S. W. Wassilew, H+ G4, p. 334, 1992; A. Klotz, Am. J. Cont. Derm., 2001, 12(1), p. 52; and A. Klotz, M. Veeger, Pharm. Ztg. 2000, 145(35), pp. 47 to 51.

This method is an in vivo test model to check the skin compatibility of various test products in direct comparison. The products to be tested are applied to the subjects in air-impermeable aluminum chambers on the volar side of their forearms on 4 consecutive days on the same test area each time. What is assessed are skin irritations having formed, using the scale specified below, and the application time 1 day after the last application of product.

R=reddening (erythema): 0=no erythema, 4=massive erythema;

S=scaling: 0=no scaling, 4=massive scaling;

F=fissures: 0=no fissures, 4=massive fissures.

The following are found as criteria for assessment:
1. the irritation $\bar{x}$ as mean value of the sum of the irritation values R, S and F of n subjects,
2. the application time $\bar{h}$ as mean value of the tolerated application time in hours of n subjects Using these two values, the relative skin compatibility (A value) can be calculated according to the following formula:

$$\bar{A} = \frac{\bar{h}}{\sqrt{\bar{x}}}$$

Thus, it is possible by means of a value to describe a relation between the application time and an irritation having formed during said time. The following Table can be used as an aid in assessing the skin compatibility of the tested products:

| A value: | |
|---|---|
| >23 | excellent skin compatibility |
| 18-23 | high skin compatibility |
| 13-18 | good skin compatibility |
| 8-13 | satisfactory skin compatibility |
| 3-8 | sufficient skin compatibility |
| <3 | insufficient skin compatibility |

Examination of Skin Dehydration Using a Corneometer

Corneometer measurement is a non-invasive, capacitive measuring procedure for rating the moisture condition of the uppermost skin layers of the Stratum corneum. In subjects with healthy skin, said condition is largely determined by external effects.

Frequent skin cleansing gives rise to defatting of the skin and thus to a reduction of moisture in the uppermost skin layers. Reduction of the moisture content of the skin represents a deterioration of the skin condition, causing an increased risk of eczema. This effect can be detected by measuring techniques using a Corneometer, e.g. the CM 825 from Courage & Khazaka Electronic GmbH, Cologne.

The initial values ($C_0$) are determined prior to starting the test, and the final values ($C_n$) are determined upon completing the test.

The change in skin moisture C is calculated as follows:

$$C = (C_n - C_0)$$

Negative values indicate an increase of skin moisture, and positive values indicate a reduction of skin moisture.

Examination of Cleansing Power Using the Hand Wash Test

The test model of the hand wash test using standardized dirt or lacquer provides information as to the cleansing effect of the products to be examined. For practical relevance, all test persons must have a characteristic skin structure of their palms as a result of manual labor. Using one product at a time, the following test is performed in the morning and in the afternoon:

Test Performed with Water
  0.5 g of dirt (model dirt, practical dirt or lacquer) is spread onto the palm and back of the hand and rubbed;
  allow to dry for 1.5 minutes;
  1.2 g of test product is applied and rubbed in;
  add 1 ml of water and wash for 30 seconds;
  again, add 1 ml of water and wash for 30 seconds;
  rinse under flowing cold water;
  visual assessment of the residual soiling (RS) on the back and palm of the hand in accordance with the scale below.

Test Performed without Water
  0.5 g of dirt (model dirt, practical dirt or lacquer) is spread onto the palm and back of the hand and rubbed;
  allow to dry for 1.5 minutes;
  1.2 g of test product is applied and rubbed in;
  remove soiling on palms together with product by means of a cellulose paper;
  visual assessment of the residual soiling (RS) on the back and palm of the hand in accordance with the scale below.

0=clean; 5=no cleansing effect (0.5 gradations are possible)

The percent cleansing effect is calculated according to the following formula:

$$\text{Cleansing effect} = \frac{10 - (\overline{RS}_{palm} + \overline{RS}_{back})}{10} \times 100 \ (\%)$$

$\overline{RS}_{palm}$=mean value of residual soiling on palm in n measuring series (subjects)

$\overline{RS}_{back}$=mean value of residual soiling on back of hand in n measuring series (subjects)

As the determination of the cleansing effect has a broader variation range due to the test method, an absolute deviation of 5% between two measuring series is admissible.

Composition of a Suitable Model Dirt:

| | |
|---|---|
| Motor oil | 54.15% |
| Vaseline | 18.05% |
| Adeps lanae | 18.05% |
| Graphite | 3.61% |

-continued

| | |
|---|---|
| Flame soot | 5.42% |
| Iron oxide (Fe$_2$O$_3$) | 0.72% |

EXAMPLES

Skin and hand cleansing agents were produced according to the compositions specified in Table 1 by stirring together all components at 70° C. at maximum, using the cold—cold, hot-cold or hot—hot processes conventional in cosmetics. The agents were characterized with respect to their skin compatibility, skin dehydration and cleansing effect on model dirt and lacquer.

Compared to the comparative formulation No. 7 free of solvent, which was produced according to WO 99/06021, the Examples 1 to 6 of formulations according to the invention have comparable, high skin compatibility in the skin compatibility test described above and comparable skin dehydration upon cleansing in the corneometer test. On the other hand, the skin compatibility of the Examples 1 to 6 of formulations according to the invention is clearly superior in comparison to the solvent-containing, commercially available comparative product No. 8.

Moreover, compared to the solvent-containing comparative product No. 8, the formulations 1 to 6 according to the invention show a comparable high cleansing effect on soiling from lacquer and model dirt in the standardized cleansing test described above. However, the cleansing effect of the Examples 1 to 6 of formulations according to the invention is clearly superior when compared to the highly skin-compatible, solvent-free formulation No. 7 according to WO 99/06021.

TABLE 1

| All formulation examples in wt. % | 1 | 2 | 3 | 4 | 5 | 6 | 7 | 8 |
|---|---|---|---|---|---|---|---|---|
| Colza oil | 40 | 50 | 30 | 40 | — | 20 | — | — |
| Soya oil | — | — | — | — | 40 | — | — | — |
| Laureth-6 | 18 | 25 | 16 | 22 | — | 10 | — | — |
| Laureth-5 | — | — | — | — | 22 | — | — | — |
| Stabilizers | 5.2 | 5.2 | 6.7 | 5.2 | 5.2 | 7.2 | — | — |
| Petroleum distillate | — | — | — | — | — | — | — | 40 |
| Mineral oil | — | — | — | — | — | — | — | 10 |
| Sodium oleate | — | — | — | — | — | — | — | 10 |
| Trideceth-9 | — | — | — | — | — | — | — | 3 |
| Propylene glycol | — | — | — | — | — | — | 3 | 3 |
| Sodium PCA | — | — | — | — | — | — | 1 | — |
| Petrolatum | — | — | — | — | — | — | — | 1 |
| Lanolin | — | — | — | — | — | — | — | 1 |
| Octyl stearate | — | — | — | — | — | — | 3 | — |
| C$_{12}$-C$_{18}$ Pareth-5 | — | — | — | — | — | — | 3 | — |
| Sodium laureth-11 carboxylate | — | — | — | — | — | — | 2.5 | — |
| Preservative | q.s. | q.s. | q.s. | q.s. | q.s. | q.s. | q.s. | q.s. |
| Perfume | q.s. | q.s. | q.s. | q.s. | q.s. | q.s. | q.s. | q.s. |
| Water | 28 | 20 | 35 | 31 | 31 | 40 | 87 | 30 |

The invention claimed is:

1. A composition comprising:
   a) 10 to 60 wt. % of one or more triglycerides, saturated, unsaturated fatty acids and/or mixtures thereof,
   b) 5 to 40 wt. % of at least one fatty alcohol ethoxylate,
   c) 10 to 65 wt. % of water,
   wherein said composition does not contain fatty alcohol ether sulfate.

2. The composition of claim 1, which is free of organic solvents.

3. The composition of claim 1, which is free of abrasives.

4. The composition of claim 1, which further comprises 1–30 wt. % of one or more abrasive(s).

5. The composition of claim 1, which comprises up to 30% of an abrasive selected from the group consisting of at least one abrasive based on polyethylene, polyurethane, natural stone, shell meal, and wax beads.

6. The composition of claim 1, wherein the amount of a) ranges from 25–55 wt. %.

7. The composition of claim 1, wherein the amount of a) ranges from 40–45 wt. %.

8. The composition of claim 1, wherein a) is synthetic.

9. The composition of claim 1, wherein a) is a naturally-occurring fat and/or oil.

10. The composition of claim 1, wherein a) consists of at least one vegetable oil.

11. The composition of claim 1, wherein a) comprises colza oil, soya oil and/or linseed oil, or mixtures thereof.

12. The composition of claim 1, wherein b) comprises 10–35 wt. % of at least one fatty alcohol ethoxylate.

13. The composition of claim 1, wherein b) comprises 15–30 wt. % wt. % of at least one fatty alcohol ethoxylate.

14. The composition of claim 1, wherein b) comprises at least one fatty alcohol ethoxylate of general formula:

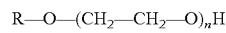

$$R-O-(CH_2-CH_2-O)_nH$$

wherein
R=saturated, unsaturated, branched or unbranched alkyl residue,
n=integer of from 1 to 11.

15. The composition of claim 1, which further comprises a viscosity building agent selected from the group consisting of at least one of an organophilic and/or hydrophilic layer of silicates, a polysaccharide, a modified polysaccharide, and an inorganic electrolyte.

16. The composition of claim 1, which further comprises at least one viscosity building agent selected from the group consisting of bentonite, cellulose, guar meal, xanthan, cellulose ether, carboxymethylcellulose, hydroxyalkylcellulose, sodium chloride and magnesium chloride.

17. The composition of claim 1, which further comprises at least one pH regulator, stabilizer, preferably cetearyl alcohol and/or hydrogenated castor oils, odorous substances preservative, preferably organic acid, particularly citric acid, antioxidant, and/or oily or aqueous care component, preferably bisabolol, Aloe vera, panthenol, and jojoba oil as cosmetic adjuvants, additives and/or active substances.

18. The composition of claim 1, which comprises 15 to 25 wt. % of laureth-6 as fatty alcohol ethoxylate.

19. A method of cleaning skin comprising applying the composition of claim 1 to skin without the additional application of water.

20. A method of cleaning skin comprising applying the composition of claim 1 to skin and the additional application of water.

21. A composition comprising:
   a) 10 to 60 wt. % of one or more triglycerides, saturated, unsaturated fatty acids and/or mixtures thereof,
   b) 5 to 40 wt. % of at least one fatty alcohol ethoxylate,
   c) 10 to 65 wt. % of water,
   wherein said composition does not contain fatty alcohol ether sulfate and/or castor oil sulfonates.

* * * * *

UNITED STATES PATENT AND TRADEMARK OFFICE
CERTIFICATE OF CORRECTION

PATENT NO. : 7,241,452 B2  Page 1 of 1
APPLICATION NO. : 10/489596
DATED : July 10, 2007
INVENTOR(S) : Veeger et al.

It is certified that error appears in the above-identified patent and that said Letters Patent is hereby corrected as shown below:

On the title page, and column 1, line 1: Item (54), the title is incorrect. Item (54) should read:

-- (54)  SKIN AND HAND CARE AGENTS --

Signed and Sealed this

Second Day of October, 2007

JON W. DUDAS
*Director of the United States Patent and Trademark Office*

UNITED STATES PATENT AND TRADEMARK OFFICE
CERTIFICATE OF CORRECTION

PATENT NO. : 7,241,452 B2
APPLICATION NO. : 10/489596
DATED : July 10, 2007
INVENTOR(S) : Marcel Veeger et al.

It is certified that error appears in the above-identified patent and that said Letters Patent is hereby corrected as shown below:

On the title page, item (57) ABSTRACT, replace in its entirety with the following:

-- The invention concerns aqueous agents for skin and hand care, compatible with the skin and having good cleansing effect. Said agents are characterized in that they contain 10 to 60 wt. % of one or more triglycerides, saturated or unsaturated fatty acids or mixtures thereof, 5 to 40 wt. % of at least a fatty alcohol ethoxylate, 10 to 65 wt. % of water, 0 to 30 wt. % of one or more abrasives, relative to the composition of the cleansing agents, and optionally one or more viscosity agents and other auxiliary agents, additives of active cosmetic agents. --.

Column 1, line 44, "Zinc pyrithione: 0.1 to 1.0 wt.-%"
 delete in its entirety, duplicate entry.

Column 2, line 10, "coconut fatty-acid" should read -- coconut fatty acid --.

Column 5, line 31, "1. the irritation $\overline{x}$ as mean value of the sum of the irritation"
 should read -- the irritation $\overline{x}$ as mean value of sum of the irritation --;
 " 2. the application time $\overline{h}$ as mean value of the tolerated"
 should read -- 2. the application time $\overline{h}$ as mean value of the tolerated --.

Column 8, line 27, "15-30 wt. % wt. % of at least one fatty alcohol ethoxylate."
 should read -- 15-30 wt. % of at least one fatty alcohol ethoxylate. --.

Signed and Sealed this

Sixteenth Day of June, 2009

JOHN DOLL
*Acting Director of the United States Patent and Trademark Office*